US00PP27646P3

(12) United States Plant Patent
Shipley

(10) Patent No.: US PP27,646 P3
(45) Date of Patent: Feb. 7, 2017

(54) TEXAS LIVE OAK TREE NAMED 'JOAN LIONETTI'

(50) Latin Name: *Quercus fusiformis*
Varietal Denomination: Joan Lionetti

(71) Applicant: Nicholas Shipley, Tucson, AZ (US)

(72) Inventor: Nicholas Shipley, Tucson, AZ (US)

( * ) Notice: Subject to any disclaimer, the term of this patent is extended or adjusted under 35 U.S.C. 154(b) by 169 days.

(21) Appl. No.: 14/120,681

(22) Filed: Jun. 17, 2014

(65) Prior Publication Data

US 2015/0366119 P1 Dec. 17, 2015

(51) Int. Cl.
*A01H 5/00* (2006.01)

(52) U.S. Cl.
USPC ..... Plt./225

(58) Field of Classification Search
USPC ..... Plt./225
See application file for complete search history.

*Primary Examiner* — June Hwu

(57) ABSTRACT

A new and distinct *Quercus fusiformis* variety named 'Joan Lionetti' is characterized by dark green colored leaves, dense upreaching crown structure, excellent adaptation to conditions prevailing in the southwestern United States, with relatively low mast production.

4 Drawing Sheets

Latin name: *Quercus fusiformis.*
Varietal denomination: 'Joan Lionetti'.

BACKGROUND OF THE INVENTION

*Quercus* is a large genus of the plant family Fagaceae consisting of approximately 600 species of trees and shrubs native to the Northern Hemisphere. In English, these plants are ordinarily referred to as oaks. Various oaks find usage for timber in the production of hardwood lumber, construction timbers and for cooperage. Oaks constitute important wildlife trees, providing habitat for many native animals as well as producing acorns used as food by both by humans and animals. Oaks mature into attractive, long lived trees frequently utilized in landscape plantings. The present invention relates to a new and distinct cultivar of *Quercus fusiformis*, an evergreen oak native from southwest Oklahoma, through Texas into northeast Mexico. *Quercus fusiformis* is also known as Texas Live Oak, Escarpment Live Oak and Plateau Live Oak. For many years, selected open pollinated seedlings of this species have been sold under the cultivar name 'Heritage' live oak. *Quercus fusiformis* is the most cold hardy Live Oak, tolerating temperatures down to −10 F. Texas Live Oak possesses excellent tolerance to alkaline, somewhat saline soils and to droughty conditions, resulting in this species being widely utilized in managed landscapes throughout the southwestern United States.

In 2003 the inventor grew out a lot of 5000 seedlings in a cultivated area near Sahuarita, Ariz. From these plants, one individual possesses the unique combination of dark colored leaves, dense crown structure, upright growth form and excellent adaptation to local conditions with low mast production which is the object of this application.

SUMMARY OF THE INVENTION

Among the features that distinguish the new *Quercus fusiformis* 'Joan Lionetti' cultivar from all other available and commercial varieties of Texas Live Oak known to the inventor are the following combination of characteristics:

dark green colored leaves, dense upreaching crown structure, excellent adaptation to local conditions and relatively low mast production, resulting in lessened debris accumulation in the landscape.

*Quercus fusiformis* 'Joan Lionetti' will be used as an ornamental or shade tree well adapted to conditions found throughout the southwestern United States.

The propagation procedure for 'Joan Lionetti' is as follows: 'Joan Lionetti' is asexually propagated from semi-hardwood cuttings. Semi-hardwood cuttings are prepared (basally deleafed, about 4 inches long) and wetted in DIP'N GRO™, then placed into a peat medium substrate in spring or summer in a humidity controlled mist greenhouse with internal temperature between 70 and 85 F. Cuttings root within about 6 weeks.

The growth rate of the 'Joan Lionetti' Texas Live Oak is medium.

The foregoing characteristics and distinctions come true to form and are established and transmitted throughout succeeding propagations. The present invention has not been evaluated under all possible environmental conditions, such that the phenotype may vary with variations in environmental conditions without a change of the genotype of the plant.

BRIEF DESCRIPTION OF THE DRAWINGS

The accompanying photographs illustrate *Quercus fusiformis* Joan Lionetti growing near Tucson, Ariz., depicted in color as nearly correct as it is possible to make in a color illustration of the character.

DETAILED PLANT DESRIPTION

Figure 1:
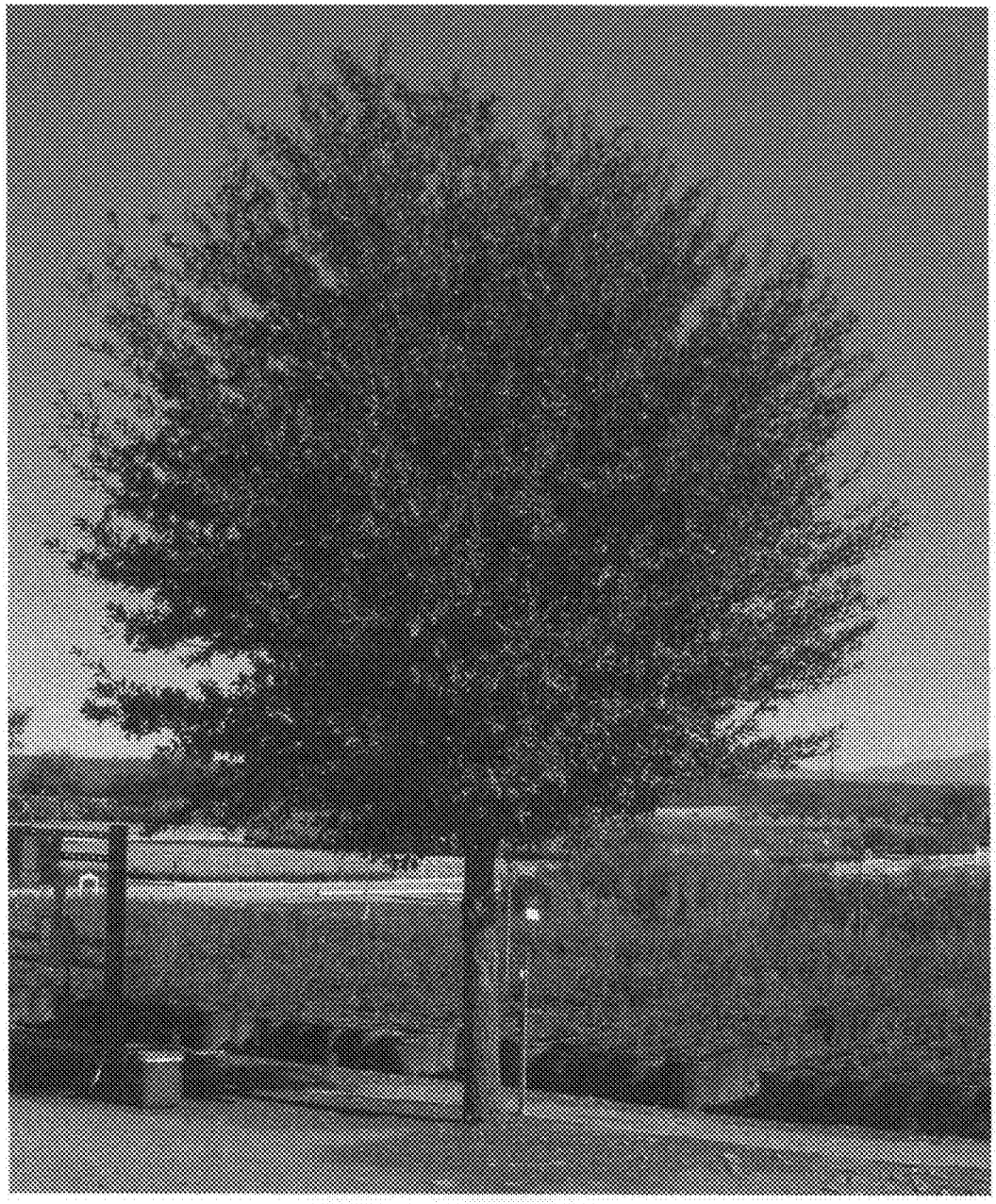
FIG. 1 shows the 9 year old original *Quercus fusiformis* 'Joan Lionetti' growing in a cultivated area near Sahuarita, Ariz.
Figure 2:
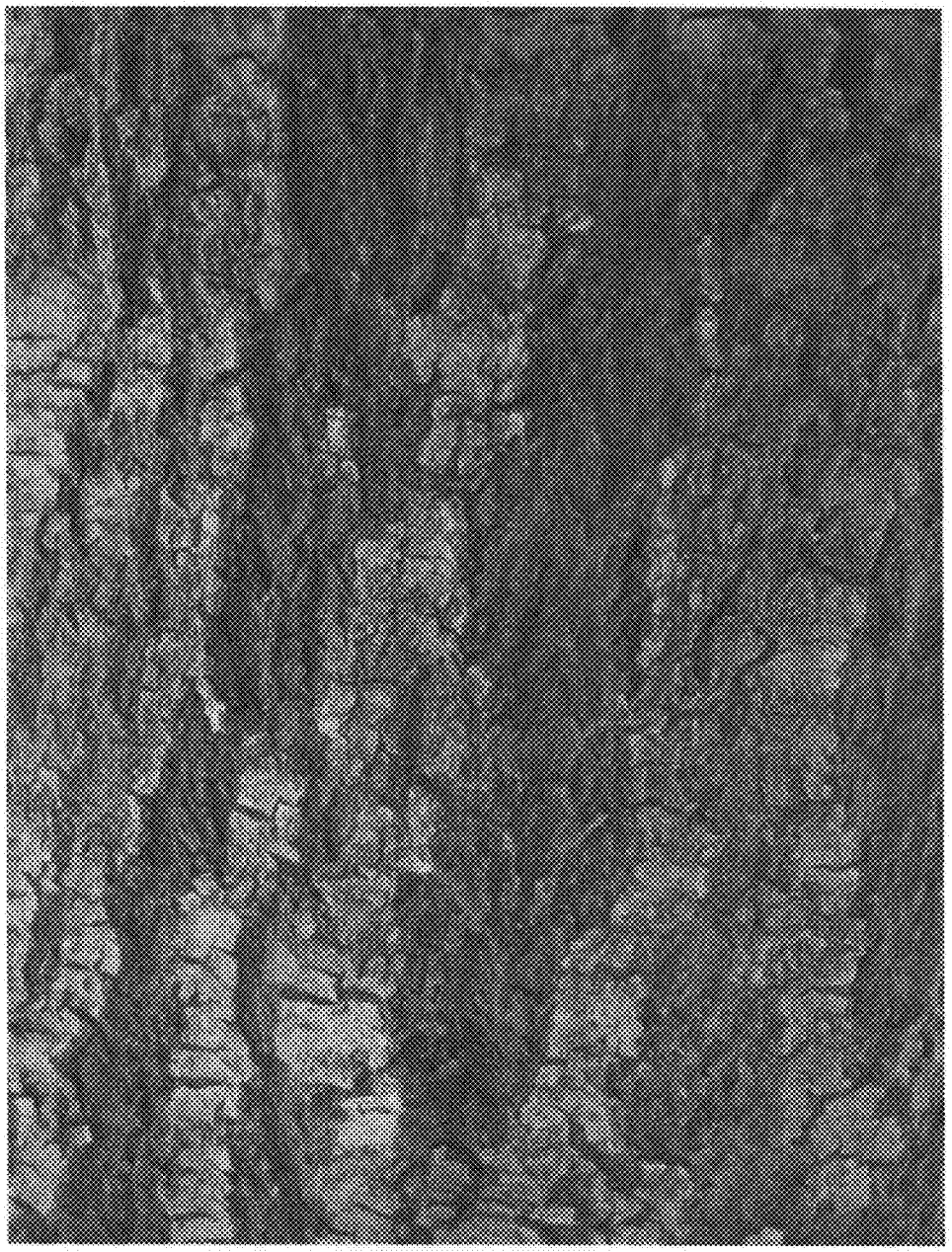
FIG. 2 is a closeup of the bark of *Quercus fusiformis* 'Joan Lionetti'.
Figure 3:
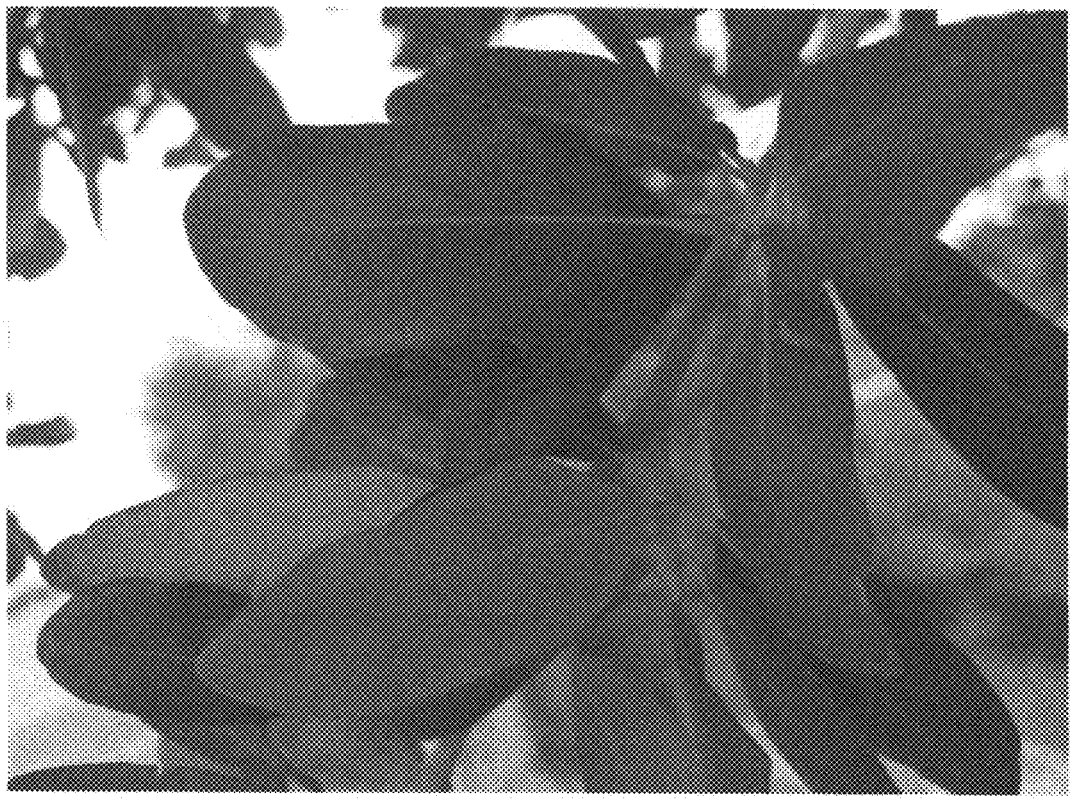
FIG. 3 is a closeup of the leaves of *Quercus fusiformis* 'Joan Lionetti'
Figure 4:
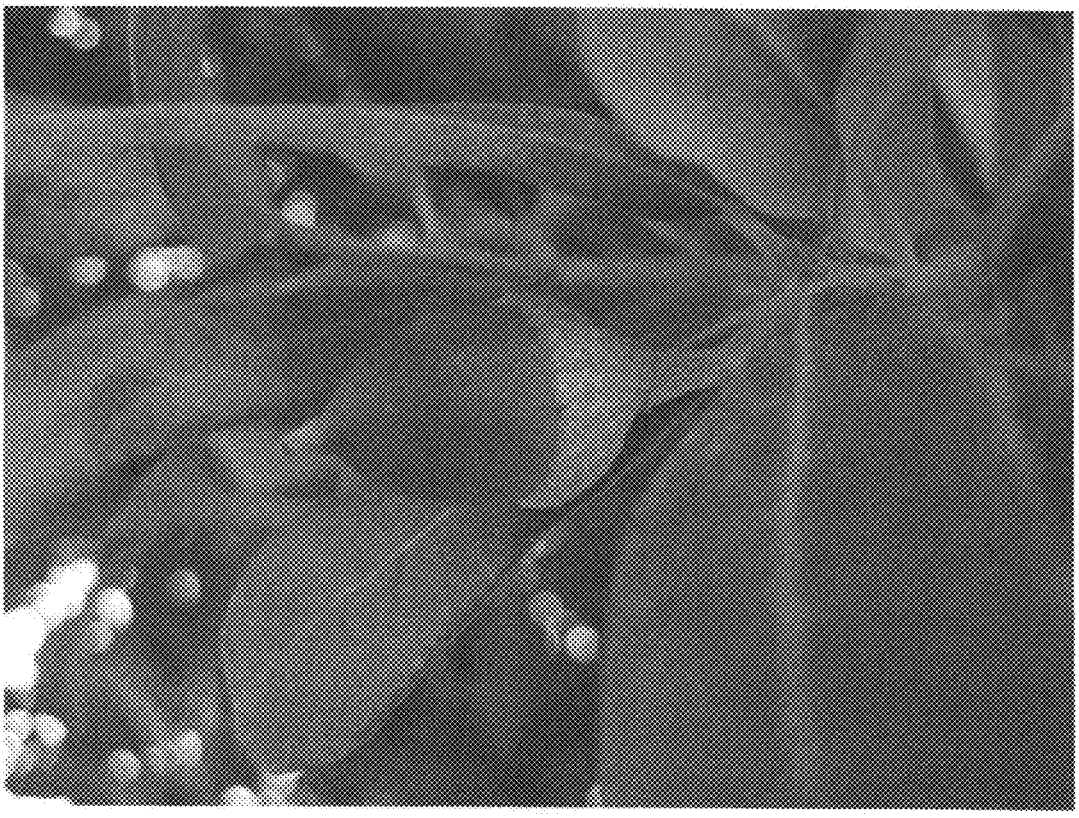
FIG. 4 is a closeup of a nearly mature acorn and associated structures of *Quercus fusiformis* 'Joan Lionetti'

The following is a detailed description of the new *Quercus fusiformis* plant based upon measurements from a 9 year old plant growing near Sahuarita, Ariz. At age 11 the tree was reexamined at age 11, Color descriptions are based upon the 5$^{th}$ edition R.H.S. Colour Chart. Color names other than common usage are as listed in *COLOR Universal Language and Dictionary of Names,* by Kenneth L. Kelly and Deane B. Judd; National Bureau of Standards special publication 440. Washington, D.C.: U.S. Department of Commerce, National Bureau of Standards, December 1976.

Plant name: 'Joan Lionetti'.

Species: *Quercus fusiformis.*

Original source plants: Open pollinated seed from cultivated *Quercus fusiformis.*

Original collection data: Seeds collected from cultivated material fall 2002.

Plant size at 9 years of age: Standard tree 18 feet tall by 12 feet wide. At age 11 the tree had grown to 22 feet tall by 20 feet wide. This gives a growth rate of about 2 ft/year under local conditions. Typical mature Texas Live Oaks generally reach around 30×30 feet at maturity. Plants grow denser, more upright and darker green in appearance than the typical range of forms normally observed in *Quercus fusiformis.*

Trunk diameter: 11 inches at 4½ feet height at age 11 years.

Bark: 1-3 year old branches from 2-5 mm in diameter color 197C, somewhat rugose.

Mature bark: Fissured, color 167D in the fissures, grading to 202A with age and finally fading to 202D on the oldest bark surfaces.

Branch angle: About 45 degrees.

Dormant buds: Spheroidal to oblate spheroid, 2 mm long× 1.5 mm diameter, imbricate, scales rounded, ciliate, nearly glabrous on surfaces, 166C.

Young, but mature stems: 197C, lanulate with small lenticels centered in longitudinal slits ⅓-⅔ mm long, stems with increasing age form an elongated reticulum, becoming rugose and glabrous.

Leaves: Alternate, abaxially cupped, (length×width (mm)) 18-67×9-35, adaxial surface (147A) nearly glabrous, somewhat lustrous with scattered stellate hairs; abaxial surface (194A) densely covered with an interlocking tomentum of fine stellate hairs; petioles color varying from 198C on shaded petioles to 175B on some sun exposed leaves, 4-7 mm long×1.25-1.5 mm thick, lanulate. Leaf shape varies from irregularly obovate to oblanceolate to elliptical. Leaf margin varies from entire to irregularly slightly undulate. Some leaves have from 1 to 5 small teeth on some of these small lobes (one per lobe). Leaf apex generally rounded, obtuse. An occasional leaf may have a small apical tooth. Leaf base varying from acute to rounded obtuse.

'Joan Lionetti' generally blooms in autumn, with fruits (acorns) maturing mostly in November under growing conditions typically found at Sahuarita, Ariz. Male flowers 1.5 mm, spheroidal just prior to anthesis, with 1-6 flowers/node in catkins 2.0-4.5 cm long, axis lanulate 138C, anthers about 0.5 mm, 4 (3-5) per flower, 159C, dehiscence lines 165A, barely exserted, calyx of 4-6 ovate, ciliate, but otherwise glabrous sepals (N144C) formed into a cup, pollen 4C; female flowers generally solitary, axillary, spheroidal, 5 mm long×2.5 mm broad; peduncle 4-5 mm long×1.5 mm thick, terete, lanate; involucre 2.5 mm broad, visually 4 ranked at flowering, color 199C; bracts lanulate, ciliate, rounded in shape, color 199C; ovary ovoid, mucronate, color 137C.

Acorn (fruit and seed): Ovoid, acuminoid 27-31 (24) mm long×12-15 (10) mm in diameter, basally N199D, distally 200A-C, surface slightly glaucous, shiny when rubbed, obscurely striate, but noticeably more striate than typical *Quercus fusiformis*, with persistent stigma, fruit basal scar raised 161D, low hemispherical, 3 mm in diameter, with 20-21 vascular bundles; involucre (cap) 8-9 ranked 7-8 mm long×11-12 mm in diameter, obconical, bracts lanulate, ciliate, basal bracts rounded-ovate, distal bracts ovate-acuminate, bract color 199C.

COMPARISONS TO RELATED *QUERCUS*

Compared to the only other commonly available Texas Live Oak, the open pollinated 'Heritage' oak, 'Joan Lionetti' is consistent with its dense, upright form, dark green color and excellent adaptability. 'Heritage' oak, while selected for plant form, is inconsistent in growth form and characteristics, color and adaptability, and a portion of all the trees in a planting commonly fail over a period of years. 'Improved Heritage' oak is expected to provide a more consistent tree in the landscape due to its clonal nature.

I claim:

1. A new and distinct *Quercus fusiformis* plant substantially as described and illustrated herein.

* * * * *